United States Patent [19]
Jakobsen et al.

[11] Patent Number: 5,786,891
[45] Date of Patent: Jul. 28, 1998

[54] METHOD AND APPARATUS FOR DETECTING DEFECTS IN AN OPTICAL FIBER COATING

[75] Inventors: Christian Jakobsen, Copenhagen; Flemming Pedersen, Farum, both of Denmark; Leonardo M. Penn, Norcross, Ga.; Tracy E. Brewer, Charleston, S.C.; Aarne Karp, Hamilton Square; David H. Smithgall, East Windsor, both of N.J.

[73] Assignee: Lucent Technologies Inc., Murray Hill, N.J.

[21] Appl. No.: 815,180

[22] Filed: Mar. 11, 1997

[51] Int. Cl.⁶ .................. G01N 21/00; G01N 21/84; G01B 9/10
[52] U.S. Cl. .................. 356/237; 356/239; 356/73.1; 356/430; 250/227.29; 250/227.3; 250/227.31; 250/559.42; 250/559.43; 250/559.45
[58] Field of Search .................. 356/237, 239, 356/430, 73.1; 118/712, 670, 672; 427/10, 163.2; 65/378, 382, 485, 491; 250/227.29, 227.3, 227.31, 559.42, 559.43, 559.45

[56] References Cited

U.S. PATENT DOCUMENTS

| | | | |
|---|---|---|---|
| 4,021,217 | 5/1977 | Bondybey et al. | 65/13 |
| 4,135,902 | 1/1979 | Oehrle | 65/2 |
| 4,439,467 | 3/1984 | Kassahun et al. | 427/163 |
| 4,924,087 | 5/1990 | Bailey et al. | 356/73.1 |
| 5,172,421 | 12/1992 | Nakamura et al. | 356/73.1 |
| 5,185,636 | 2/1993 | Button et al. | 356/73.1 |
| 5,228,893 | 7/1993 | Smithgall et al. | 65/2 |

OTHER PUBLICATIONS

Cooling and Bubble–Free Coating of Optical Fibers at a High Drawing Rate, C.M.G. Jochem et al., vol. LT–4, No. 7, Jul., 1986, Journal of Lightware Technology, pp. 739–742.

*Primary Examiner*—Frank G. Font
*Assistant Examiner*—Amanda Merlino

[57] ABSTRACT

The present invention provides an optical detection system for detecting defects in an optical fiber. The system includes a light source for coupling light into the secondary coating of an optical fiber at a preselected angle with respect to the longitudinal axis of the fiber and an optical detector positioned adjacent the fiber at a preselected distance from the point at which the light is coupled into the fiber coating. In accordance with one embodiment, the light is coupled into the fiber coating at a sufficiently shallow angle with respect to the longitudinal axis of the fiber to cause the light to travel through the coating in a direction substantially parallel to the axis of the optical fiber for some distance before exiting the coating. By placing the detector a preselected distance from the coupling point, detection of light reflected from the fiber at the coupling spot is avoided and only light reflected by defects contained in the primary or secondary coating layers, or light reflected by delaminations between the primary coating layer and the fiber, will be detected by the detector.

17 Claims, 12 Drawing Sheets

METHOD AND APPARATUS FOR DETECTING DEFECTS IN AN OPTICAL FIBER COATING

TECHNICAL FIELD OF THE INVENTION

The present invention relates to a method and apparatus for detecting defects in the coating layers of an optical fiber. More particularly, the present invention relates to a detection system which can be incorporated into an optical fiber manufacturing process for optically detecting air bubbles or delaminations occurring in the coating layers of optical fibers as they are being drawn.

BACKGROUND OF THE INVENTION

The successful implementation of a light wave communication system requires high quality light guide fibers having mechanical properties sufficient to withstand the stresses to which they are subjected. Each fiber must be capable of withstanding over its entire length a maximum stress level to which the fiber will be exposed during installation and service. The importance of fiber strength becomes apparent when one considers that a single fiber failure will result in the loss of several hundreds of circuits.

The failure of light guide fibers in tension is commonly associated with surface flaws which cause stress concentrations and lower the tensile strength below that of pristine unflawed glass. The size of the flaw determines the level of stress concentration and, hence, the failure stress. Even micron-sized surface flaws cause stress concentrations which significantly reduce the tensile strength of the fibers.

Long lengths of light guide fibers have considerable potential strength, but the strength is realized only if the fiber is protected with a layer of a coating material such as, for example, a polymer, soon after it has been drawn from a preform. This coating serves to prevent airborne particles from impinging upon and adhering to the surface of the drawn fiber, which would weaken it or even affect its transmission properties. Also, the coating shields the fibers from surface abrasion, which could occur as a result of subsequent manufacturing processes and handling during installation. The coating also provides protection from corrosive environments and spaces the fibers in cable structures.

Light guide fibers are usually coated during a wet-coating process which typically involves drawing the light guide fiber through a reservoir of a liquid polymer material and then curing the liquid polymer material to harden it by exposing it to curing radiation (e.g., ultraviolet light).

During the wet coating process, air bubbles may become entrained between the fiber and the primary coating layer or within the primary or secondary coating layers. Bubbles in the fiber coating may cause several problems. Larger bubbles may extend through the coating thereby exposing the fiber to the environment and to mechanical effects, such as abrasion. Smaller sized bubbles cause losses in transmission. Bubbles may also prevent the fiber from being centered within the coating which can cause serious transmissions problems due to misalignment of the fiber cores when fibers are coupled.

Several attempts have been made in the prior art to prevent bubbles from forming in the fiber coating. In one method, the fiber is advanced through an opening in a baffle plate positioned in a reservoir to alleviate or substantially eliminate entrapment of air and consequent bubble formation in the fiber coating. Bubbles are stripped from the region about the fiber due to a hydrodynamic pressure increase in the fluid pressure as the fiber passes through the constriction in the fluid path caused by the baffle plate. Pressure changes are made by changing the geometry of the arrangements such as, for example, the size of the baffle plate opening.

Another coating technique is disclosed in Ohls, U.S. Pat. No. 4,246,299. A fiber is passed through an applicator having a die body that defines a small, vertically orientated, longitudinal tapered passage having a reservoir disposed about it. A series of radial ports provide fluid communication between the reservoir and the passage. Turbulence within the coating material, which causes entrapment of air bubbles, is reduced by maintaining the level of coating material in the passage.

C. M. G. Jochem and J. W. C. Van der Ligt, in an article entitled "*Cooling and Bubble-Free Coating of Optical Fibers at a High Drawing Rate*", Journal of Lightwave Technology, Vol. LT-4, No.7, July, 1986, disclose a method for preventing air bubbles from forming in optical fibers during the wet coating process by using force coating. After the fiber is drawn from the perform heated by the draw furnace, the fiber is passed through a water-cooled tube made of a heat-conducting material such as aluminum. The tube is provided with special locks at the top and the bottom to prevent air from entering the tube as much as possible. The tube is filled with a gas which transfers heat from the fiber to the inner wall of the water-cooled tube. The inlet tube of the force-feed coating applicator is made of a material that is not wetted by the liquid acrylic. During the coating process, coating liquid is automatically fed into the coating applicator in such a way that the inlet tube is just filled so that the liquid surface is perpendicular to the fiber axis. This prevents a downward meniscus from being formed. The force-feed coating applicator thus is designed to avoid problems associated with open-cup coating applicators wherein air may be drawn into the liquid coating material contained in the open-cup coating applicator as the fiber is drawn into it.

Although the techniques discussed in the foregoing may be successful in reducing the number of air bubbles contained in the coating layers surrounding an optical fiber, these techniques are not capable of completely preventing air bubbles from forming in the coating layers. Therefore, a need exists for a method of detecting when bubbles have formed in the coating layers during the optical fiber manufacturing process and for controlling the manufacturing process in accordance with the detection of bubbles to prevent or minimize their formation in the future. Ideally, such a detection system should be non-contact in order to reduce the possibility of abrading the fiber coating.

It is generally known in the industry to monitor optical fibers as they are being drawn during the manufacturing process to determine whether defects exist in the optical fibers. However, such techniques generally are directed to monitoring the optical fibers themselves, rather than the coating layers, to determine whether defects such as cracks or holes exist in the optical fibers.

It is also generally known to remove the defective optical fiber and/or to control the manufacturing process in accordance with the defects detected to prevent or minimize defects. For example, Bondybey et al, U.S. Pat. No. 4,021, 217, discloses a system for detecting optical fiber defects to determine the tensile strength of optical fibers as they are being manufactured and for adjusting the drawing conditions of the manufacturing process to eliminate, or reduce, the severity or number of defects. The apparatus disclosed in Bondybey et al. projects a focused beam of monochromatic light onto an optical fiber in a direction perpendicular to the axis of the fiber as it is being drawn. A photodetector, such as a photomultiplier, is positioned off axis with respect to the direction in which the light is projected onto the optical fiber so that it receives only scattered light unique to defects contained in the fiber. The output of the detector is received by an electrometer strip chart recorder which plots a scattering trace corresponding to the light detected. The peaks in the scattering trace correspond to defects in the optical fiber.

Button et al., U.S. Pat. No. 5,185,636, discloses a method for detecting defects such as holes in a fiber. The apparatus utilizes a laser for projecting a beam of light onto the optical fiber in a direction perpendicular to the axial direction of the fiber. Two optical detectors are positioned on each side of the optical fiber at an angle with respect to the direction of the laser beam being projected onto the optical fiber. As a result of the coherence and monochromaticity of the laser beam, interference patterns are created in the far field which are detected by the optical detectors. Holes contained in the optical fiber result in fewer fringes in the interference patterns created in the far field. The apparatus analyzes the interference patterns by a variety of techniques to determine the presence of a hole in the optical fiber and can also monitor the growth of a hole over time. The apparatus can be used in conjunction with a control system which controls the drawing of optical fibers.

Button et al., also discloses that a plurality of light sources must be used in order to ensure that light passes through the entire fiber, i.e., so that no blind spots exist. This is intended to ensure that light will be reflected off of holes contained at any location within the optical fiber and thus will be detected by the optical detectors. Spatial frequency spectra are generated based on the output of the light detectors and the spectra are analyzed to determine whether a hole exists in the optical fiber.

The systems disclosed in Button et al. and Bondybey et al. are not well suited for detecting and distinguishing defects in the primary and secondary coatings of an optical fiber because those systems are configured such that defects contained in the fiber core will be detected and no provision is made for distinguishing between defects existing in the fiber core and defects existing the fiber coatings. Accordingly, a need exists for a non-contact detection system which detects defects contained in the primary or secondary coating layers of the optical fiber and delaminations between the primary coating layer and the fiber itself. A need also exists for a system which detects defects in optical fibers in real time as the fibers are being manufactured and which controls the manufacturing process to eliminate future defects and to separate defective fiber from non-defective fiber.

SUMMARY OF THE INVENTION

The present invention provides an optical detection system for detecting defects in an optical fiber. The system comprises a light source for coupling a beam of light into the coating layer of an optical fiber at a coupling spot along the optical fiber. The light source is positioned so that the beam of light is coupled into the coating layer at a preselected angle with respect to the longitudinal axis of the optical fiber. An optical detector is positioned adjacent the optical fiber a predetermined distance away from the coupling spot. The coupling spot is between the light source and the optical detector. By separating the optical detector from the coupling spot by a predetermined distance, detection of light reflected at the coupling spot from the outer surface of the coating layer is avoided. The optical detector receives at least a portion of the light coupled into the coating layer by the light source as the light coupled into the coating layer is reflected outward from the optical fiber by defects existing in the coating layer. A signal processor is electrically coupled to the optical detector for receiving an output signal from the optical detector and for processing the output signal to determine whether or not one or more defects have been detected.

In accordance with a first embodiment, the light is coupled into the fiber coating at a sufficiently shallow angle with respect to the longitudinal axis of the fiber to cause the light to travel through the coating in a direction substantially parallel to the axis of the optical fiber for some distance before being attenuated by the coating. The angle at which the light is projected onto the fiber is selected in accordance with Snell's Law, and preferably is in the range of 50° to 30°. When defects such as air bubbles or delaminations are present in the coating layers, the light will be reflected out of the coating layers by the defects and away from the fiber. By placing the detector a preselected distance from the coupling point, detection of light reflected from the fiber at the coupling spot is avoided and only light reflected by defects contained in the primary or secondary coating layers, or delaminations between the primary coating layer and the fiber, will be detected by the detector. The output of the detector is processed and analyzed to determine whether or not defects, such as air bubbles and/or delaminations, have been detected. Based on this determination, the manufacturing process of the fiber can be controlled to prevent additional defects from forming.

In accordance with the first embodiment of the present invention, a laser is used as the light source for projecting light into the fiber coating. The laser projects a laser beam into the coating, preferably at an angle of approximately 15 with respect to the outer surface of the secondary coating. The coupling spot will be located between the laser and the optical detector approximately 1 cm from the detector. The laser preferably is modulated by a square-wave transistor-transistor logic (TTL) signal having a minimum value of 0 volts and a maximum value of +5 volts. The laser is modulated at a predetermined rate which is sufficient for the speed at which the fiber is being drawn. The TTL signal preferably is generated by a processor which receives the output of the optical detector. In order to sample the fiber properly, the processor compensates for changes in the output of the detector caused by on and off switching of the laser. In accordance with one embodiment, this is accomplished by taking the difference between the output of the detector when the TTL signal is low and the output of the detector when the TTL signal is high and averaging the differences over a number of cycles of the TTL signal. This value is then analyzed to determine whether defects, such as air bubbles or delaminations, have been detected.

In accordance with a second embodiment of the present invention, the laser is modulated with a square wave in the manner described above with respect to the first embodiment. However, in accordance with the second embodiment, synchronous detection is used to compensate for differences in the voltage level output from the detector caused by the on and off switching of the laser. Generally, the sampling of the optical detector is synchronized with the on and off switching of the laser to compensate for differences in the output of the detector resulting from modulation of the laser.

In accordance with another embodiment of the present invention, the light is projected onto the optical fiber in a direction approximately perpendicular to the longitudinal axis of the optical fiber. Light reflected out of the fiber is detected by a high-speed photodetector. The output of the photodetector is processed and analyzed, preferably in real time, to determine whether defects, such as air bubbles or delaminations, have been detected. A processing means determines the type of defect detected by the photodetector by analyzing the levels of light detected and the period of time over which particular light levels are detected.

DETAILED DESCRIPTION OF THE INVENTION

Figure 1:
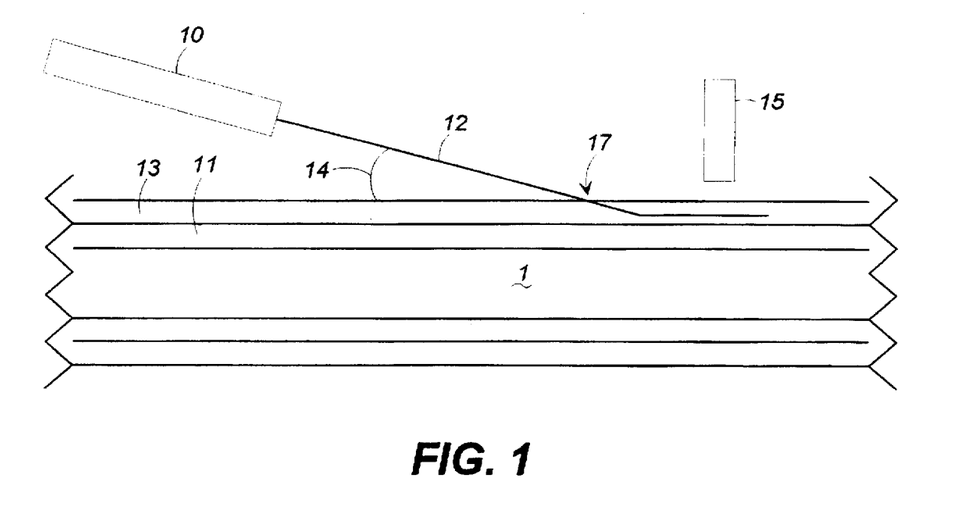
FIG. 1 is a block diagram of the bubble detector of the present invention in accordance with the preferred embodiment.

FIG. 1 illustrates a preferred embodiment of the present invention for detecting bubbles in the primary and secondary coating layers of an optical fiber and delaminations between the primary coating layer and the fiber itself. Generally, an optical fiber is comprised of the fiber 1, a primary coating layer 11 and a secondary coating layer 13. The present invention comprises a light source 10, which preferably is a laser, and an optical detector 15, which preferable is a photodiode. In accordance with the preferred embodiment of the present invention, a coherent beam of substantially monochromatic light 12 is projected by laser 10 at a preselected angle 14 onto the secondary coating layer 13 of an optical fiber. The location 17 at which the light 12 is coupled into the secondary coating layer 13 of the fiber is a preselected distance d from optical detector 15, as discussed in more detail below with respect to FIGS. 6A and 6B. Preferably, the light source 10 is a 13 mW, 635 nm, diode laser sold by Power Technology, Inc. of Ark. The optical detector 15 preferably is a silicon photodiode with a built-in amplifier sold by Radio Parts of Denmark.

The angle 14 generally is in the range of approximately 5° to approximately 30° and preferably is approximately 15°. The angle 14 preferably is sufficiently shallow to cause the light to be refracted such that it travels through the primary and secondary coatings in a direction substantially parallel to the longitudinal axis of the fiber. The manner in which this angle is selected is discussed in detail below with respect to FIGS. 6A and 6B. Bubbles contained in the primary and secondary coating layers 11 and 13, respectively, and delaminations between the primary coating layer 11 and the fiber 1 will reflect light into detector 15, which preferably comprises a lens (not shown) for focusing the light onto a photodetector (not shown) contained in optical detector 15.

Figure 2:
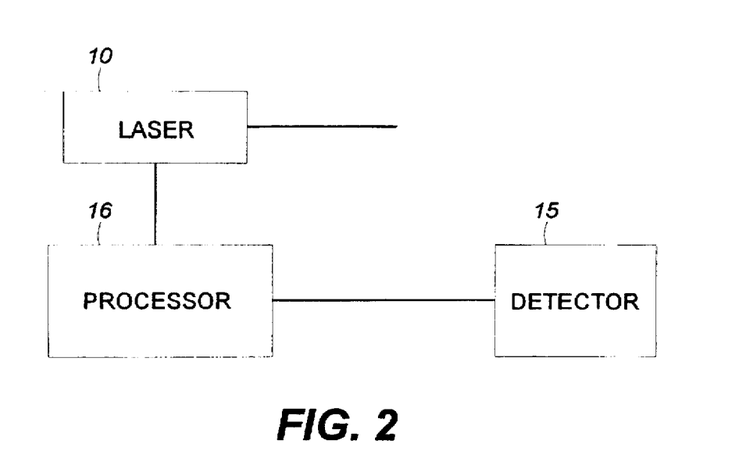
FIG. 2 is a block diagram of the bubble detector circuitry of the present invention in accordance with the preferred embodiment.

FIG. 2 illustrates a block diagram of the preferred embodiment of the bubble detector of the present invention. A processor 16, which may comprise a microprocessor and other circuit components, modulates the laser 10 with a square wave. In accordance with one embodiment of the present invention, the processor 16 generates a TTL signal having a maximum value of +5 volts and a minimum value of 0 volts. Processor 16 receives the output from detector 15 and processes the output to determine whether bubbles or delaminations exist. In accordance with a determination that bubbles or delaminations exist, the processor 16 can provide information to the manufacturing process (not shown) for adjusting parameters of the manufacturing process to prevent bubbles or delaminations from occurring in the future.

In accordance with a first embodiment of the present invention, the processor 16 averages the output of detector 15 over a predetermined number of cycles of the square wave used to modulate laser 10 in order to compensate for changes in the output of detector 15 caused by differences in the amount of light detected by detector 15 when the laser 10 is off and when it is on.

Figure 3:
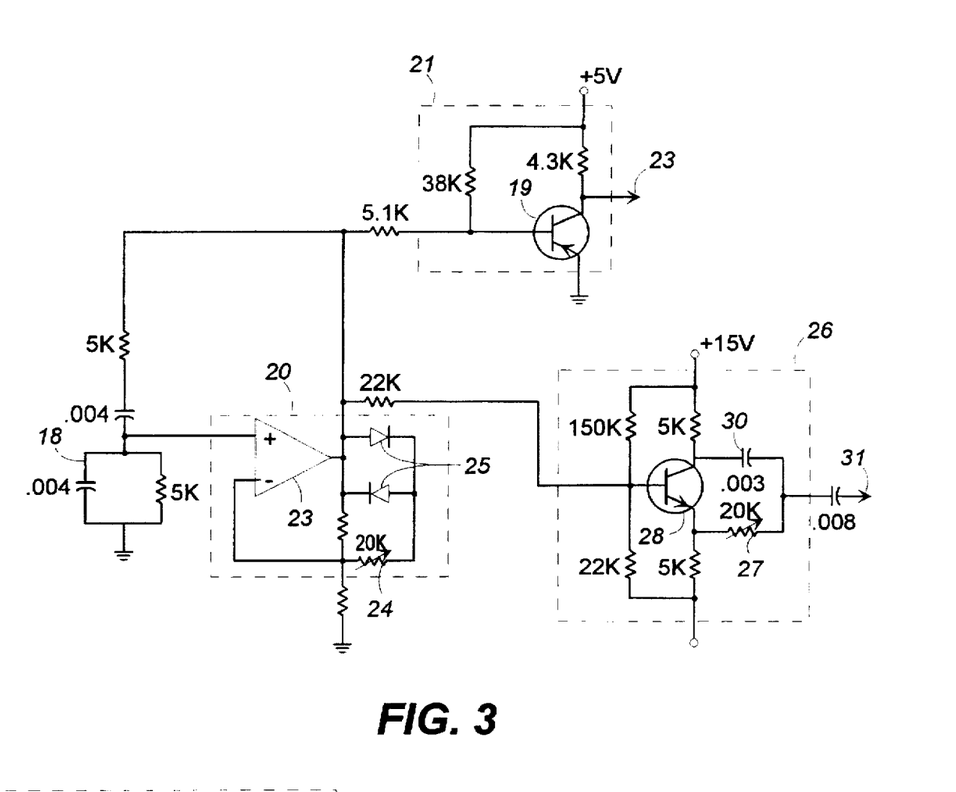
FIG. 3 is a schematic diagram of the electrical circuitry for generating a square wave for modulating the laser and for generating a sampling signal for synchronous sampling of the optical detector.

FIG. 3 illustrates a circuit diagram of an alternative embodiment of the present invention for generating the TTL signal for driving laser 10 and the trigger signal for providing synchronous sampling of the detector. An oscillation circuit 18 produces an oscillating waveform which is output to a laser driving circuit 21 and to a clamping circuit 20. The laser driving circuit 21 comprises a transistor 19 which is driven into saturation by the oscillating waveform to produce a square wave at collector 23 of transistor 19. The square wave is provided to laser 10 for driving the laser.

The oscillating waveform produced by oscillation circuit 18 is provided to the noninverting input of operational amplifier 23 of clamping circuit 20. In addition to operational amplifier 23, the clamping circuit 20 comprises a pair of diodes 25 and a potentiometer 24 which cooperate to clamp the signal fed back to operational amplifier 23 such that the signal provided to phase shift circuit 26 is a smooth sinusoidal signal. Phase shift circuit 26 comprises a potentiometer 27 connected to the emitter of transistor 28 and connected in parallel with a capacitor 30. The capacitor 30 is connected to the collector of transistor 28. The phase of the signal 31 output from phase shift circuit 26 can be altered by adjusting potentiometer 27.

Figure 4:
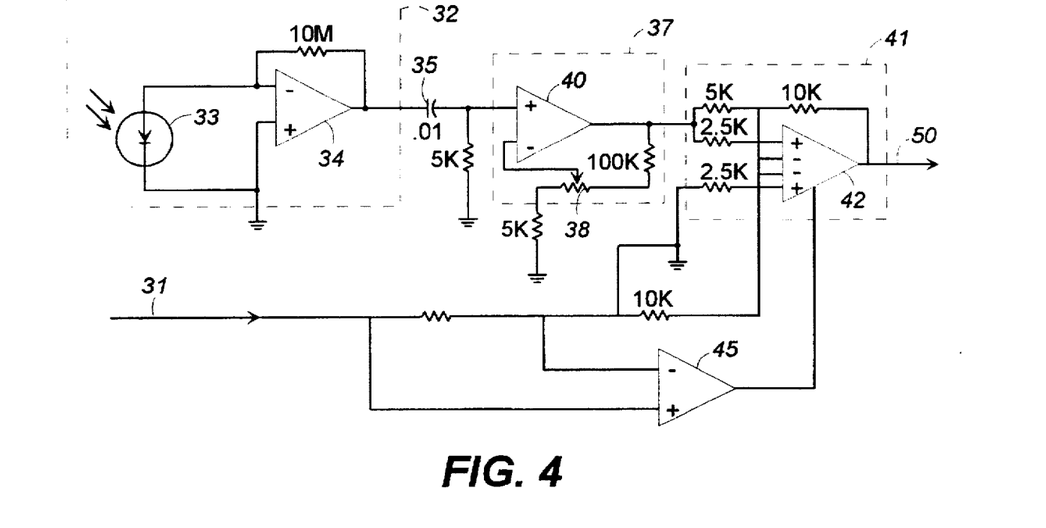
FIG. 4 is a schematic diagram of the optical detector and sampling circuitry in accordance with one embodiment of the present invention.

FIG. 4 illustrates the synchronous detection circuitry which receives the output signal 31 of phase shift circuit 26.

An optical detection circuit 32 comprises a photodiode 33 which receives light reflected by bubbles and delaminations and produces an output voltage signal in response to the light detected. The output of photodiode 33 is input to operational amplifier 34 which amplifies the signal. The detection circuit 32 is coupled by a capacitor 35 to an amplification circuit 37 which comprises a potentiometer 38 for adjusting the gain of amplifier 40 to a suitable level. The capacitor 35 filters out the dc light detected by photodiode 33. The output of amplifier 40 is input to synchronous detector circuit 41, which preferably comprises an AD630 integrated circuit 42 which is designed to produce a dc signal proportional to the amount of light detected by photodiode 33. The output 31 of phase shift circuit 26 is used to switch the AD630 integrated circuit 42 on an off, which ensures that the output of photodiode 33 is sampled at the proper time. The output 31 is provided to amplifier 45 which amplifies the signal to a level suitable for switching the AD630 integrated circuit 42 off and on.

Figure 5:
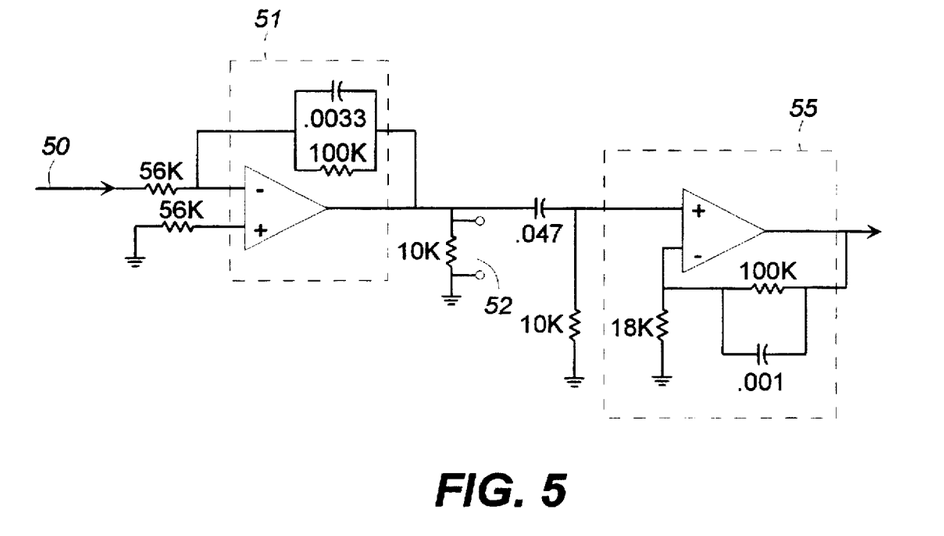
FIG. 5 is a schematic diagram of circuitry for receiving the sampled detector output and for integrating and differentiating the sampled detector output for driving a bar graph display and a nixi-type display, respectively.

The output signal 50 of the detection circuitry of FIG. 4 is provided to an integrator circuit 51 which integrates the signal to produce an output voltage across resistor 52. The output signal across resistor 52 may be provided to a bar graph display device which displays LED bars to an operator which indicate whether bubbles or delaminations are being detected and, if so, the frequency of occurrence and/or the size of the bubbles or delaminations. The signal output from integrator circuit 51 is also provided to a differentiator circuit 55 which takes the derivative of the integrated signal and provides an output signal to a nixi-type display. The nixi-type display comprises a circle of LEDs, only one of which is lit at any particular time. Events which are too short to be picked up by the bar graph display will cause the nixi display to advance the LED lit by one, thus allowing short events, e.g., the presence of a single bubble or a small group of bubbles, to be observed by an operator.

In response to a determination by the operator that bubbles have been detected, the operator can adjust the manufacturing parameters to eliminate the bubbles or to prevent bubbles from forming in the future. For example, the operator may decrease the coating pressure of the wet coating process by regulating a pump which provides coating material to a coating die. In accordance with an alternative embodiment of the present invention, the output signal 50 of detection circuitry 41 is provided to a processor, such as processor 16 shown in FIG. 1, which processes the signal and provides control signals to the manufacturing process to automatically control parameters of the manufacturing process in real time to eliminate bubbles and delaminations.

When bubbles or delaminations have been detected, or when the number and/or size of the bubbles detected has exceeded a preselected threshold, the fiber being drawn may be switched from a first take-up roll (not shown) to a second take-up roll (not shown) such that the "good" fiber is separated from the "bad" fiber. This can be done by an operator or it can be accomplished automatically by processor 16 and suitable machinery (not shown). The manner in which this may be accomplished will be apparent to those skilled in the art. The bubble detector of the present invention preferably is mounted on a draw tower at a location along the manufacturing line after the primary and secondary coating layers have been applied.

Figure 6A:
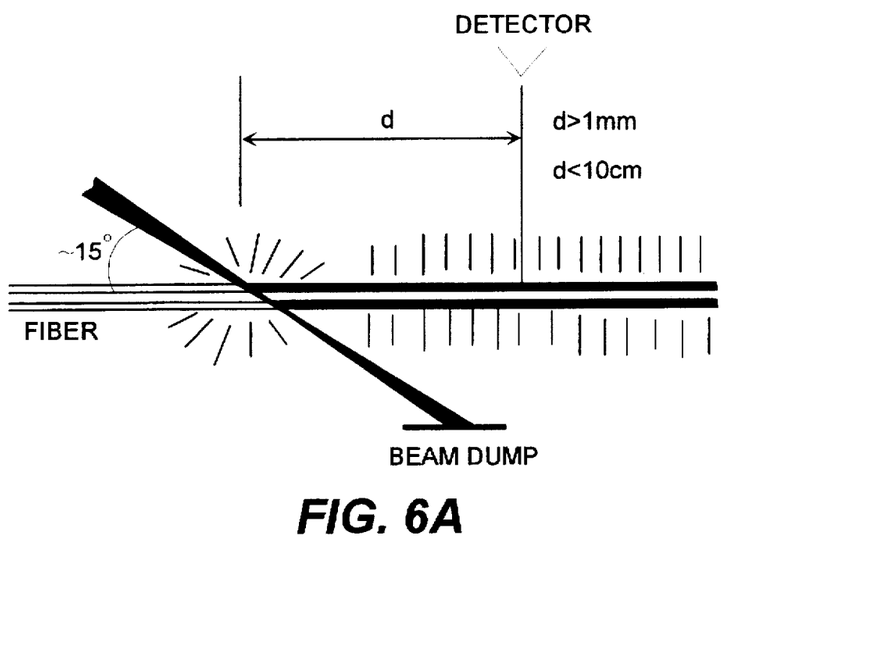
FIGS. 6A and 6B illustrate the spatial relationship between the coupling point and the optical detector and the difference between light received by the optical detector when bubbles are present and when bubbles are not present, respectively.
Figure 6B:
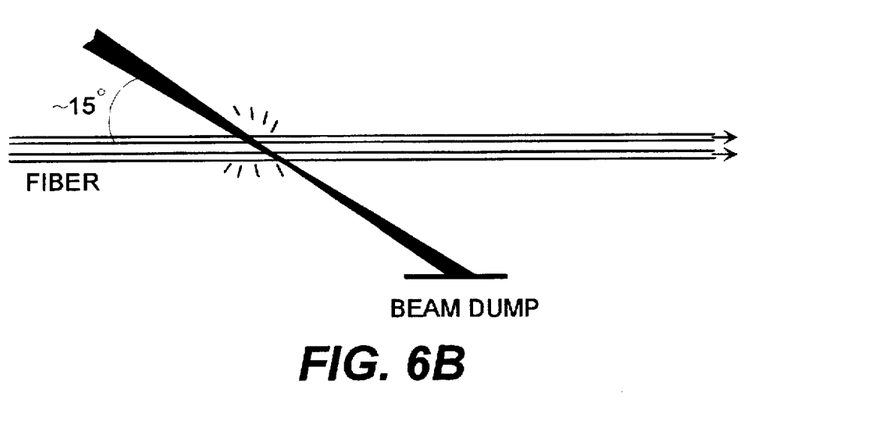

FIGS. 6A and 6B demonstrate the importance of the spatial relationship between the coupling spot and the detector. In accordance with this embodiment of the present invention, it has been determined that the optical detector should be located a distance d ranging from approximately 1 mm to approximately 10 cm from the coupling point, as shown in FIG. 6A. This relationship ensures that light reflected at the coupling point from the outer surface of the fiber coating will not be picked up by the detector. The angle at which the light is projected onto the secondary coating of the optical fiber preferably is within the range of 50° to 30°, and preferably is approximately 15°. However, this angle will depend on the refractive index of the coating material. The relationship between the angle of projection and the index of refraction of the coating is defined by the well known law of refraction, also known as Snell's Law. Snell's Law is stated as: $\sin\theta_1/\sin\theta_2 = n_2/n_1$, where $\theta_1$ is the angle between the normal to the surface of the coating and the light ray, $\theta_2$ is the angle between the refracted ray and a line continuing from the normal below the surface of the coating ($\approx 90°$), $n_1$ is the refractive index of air ($\approx 1.0$), and $n_2$ is the refractive index of the coating layer ($\approx 1.5–1.7$). Since $\theta_2$, $n_1$ and $n_2$ are known, $\theta_1$, the angle of incidence of the light ray being projected onto the fiber, can be easily determined. Once $\theta_1$ is determined, the angle of projection (indicated by numeral 14 in FIG. 1) is calculated by subtracting $\theta_1$ from 90°. Once the light is coupled into the coating layers, the light will travel within the coating layers until either the light is attenuated by the coating layers, or it is reflected out of the coating layers by defects therein.

As shown in FIG. 6A, when bubbles or delaminations are present, a portion of the light projected onto the coating layer is reflected by the bubbles or delaminations through the fiber coating and out of the coating toward the detector. FIG. 6B demonstrates that when bubbles or delaminations are not present, light projected onto the coating layer passes through the fiber to a beam dump which absorbs the light. The light also passes through the coating layers in the axial direction of the fiber, with virtually no light being reflected or refracted toward the detector. It should be noted that the detector will even detect the defects located on the opposite side of the optical fiber from the detector. This is because the light from the light source floods the coating layers, sending light around the entire circumference of the fiber.

Figure 7A:
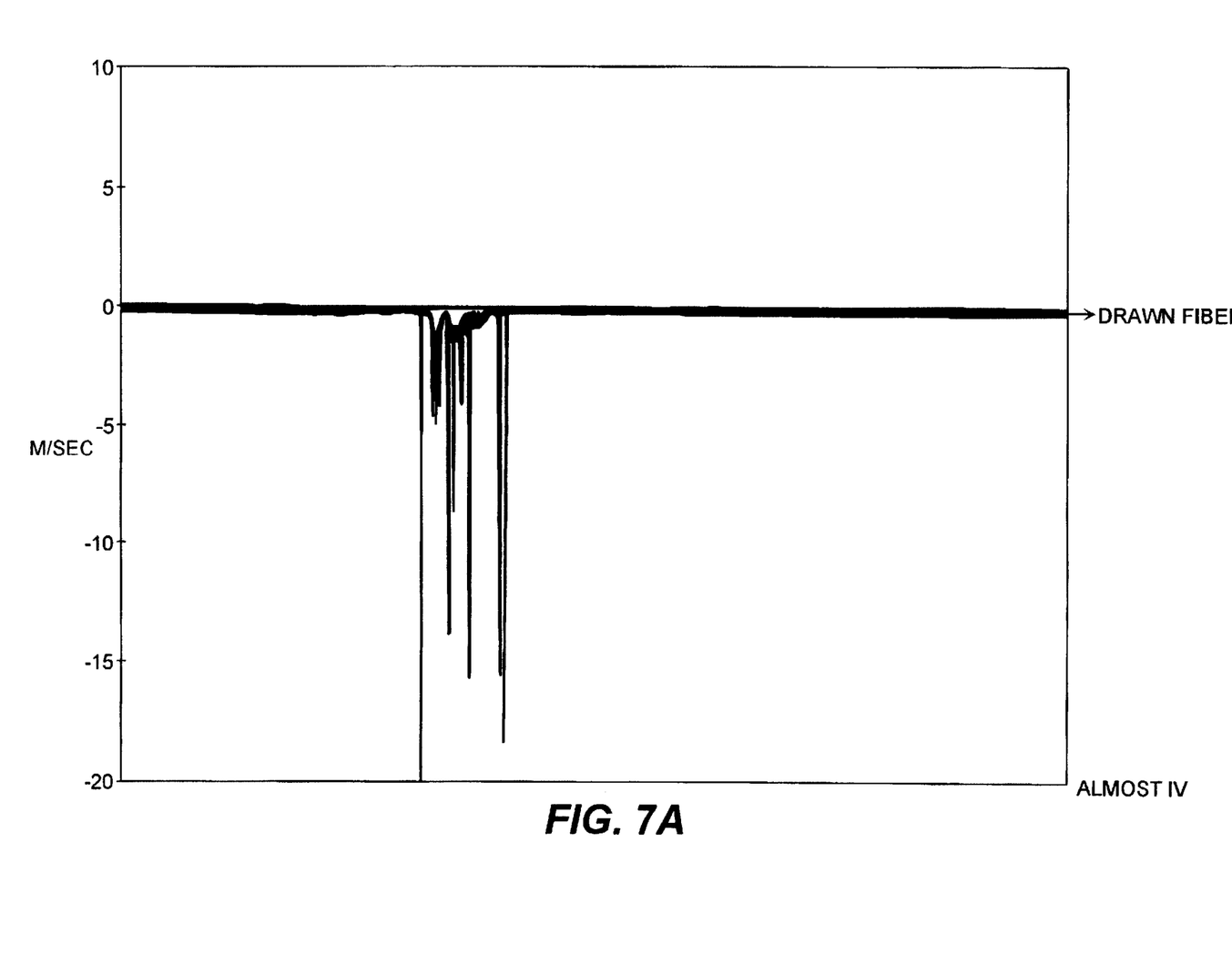
FIGS. 7A–7C graphically illustrate the relationship between the draw speed and the occurrence of bubbles or delaminations.
Figure 7B:
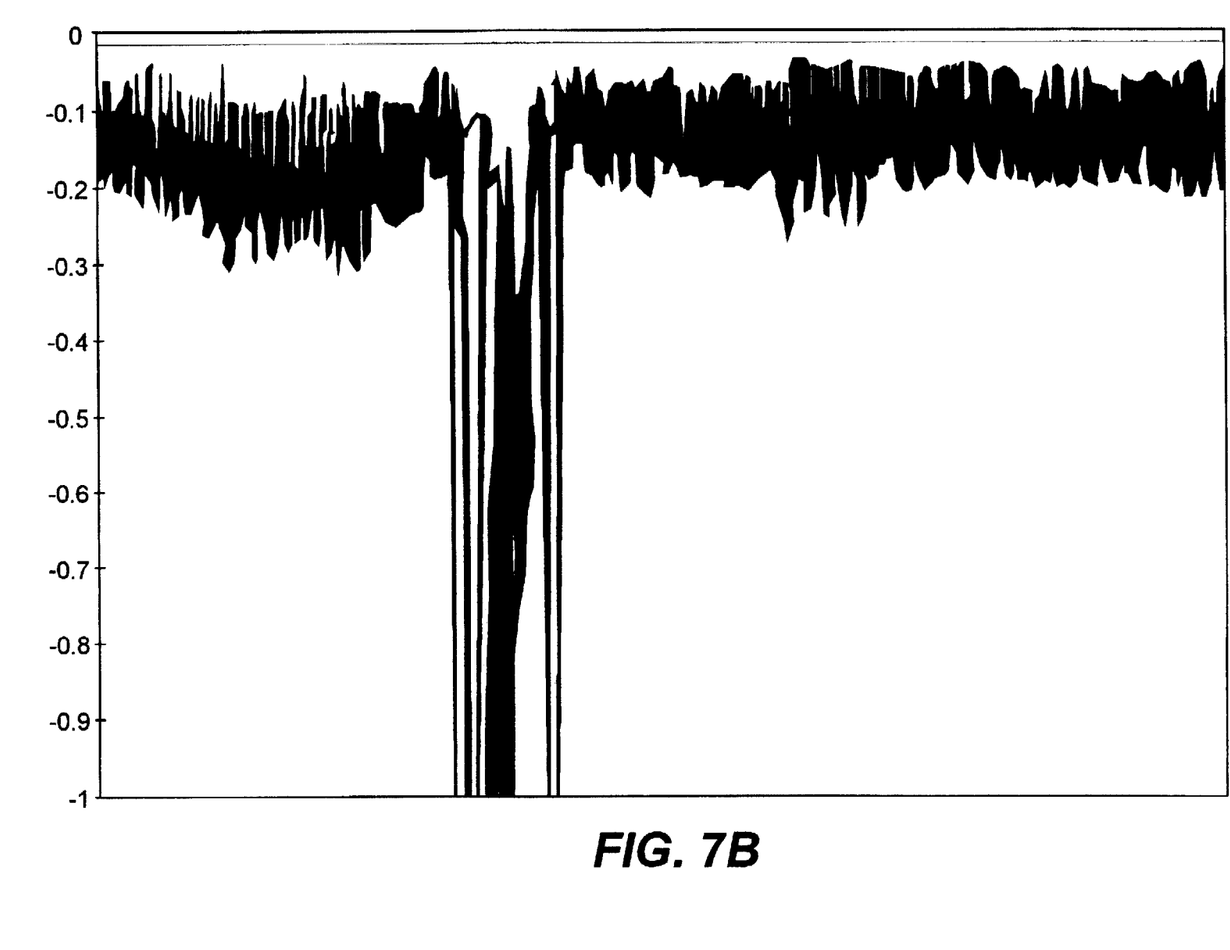
Figure 7C:
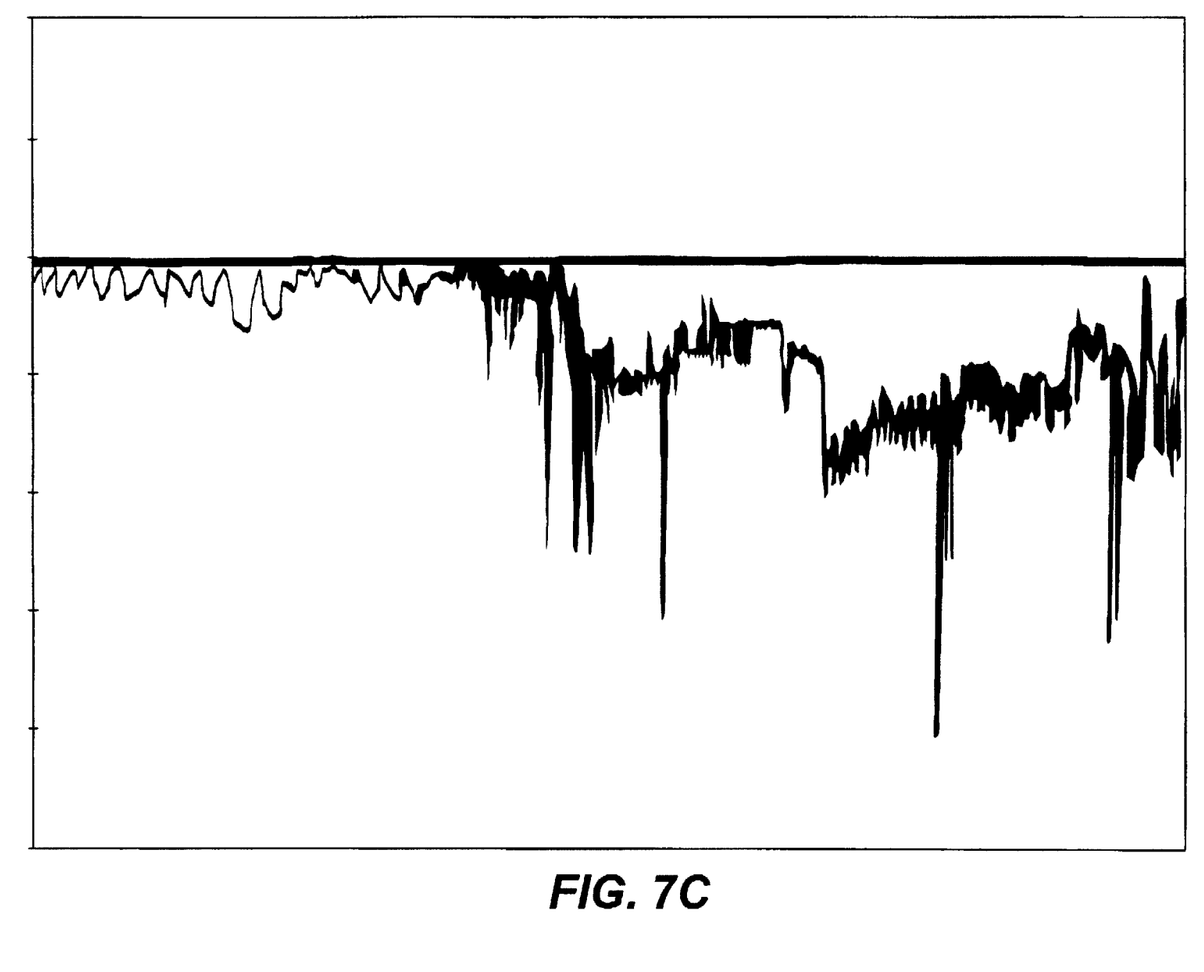

FIGS. 7A–7C illustrate the relationship between the draw speed of the fiber and the formation of bubbles or delaminations. In FIG. 7A, the upper trace represents draw speed and the lower trace represents the output of the detection circuitry. FIG. 7A demonstrates that most of the bubbles or delaminations occur at start up as the draw speed is being increased. The output of the detection circuitry is shown to be approximately −1 volt at start up, which corresponds to the largest magnitude of the detection signal. FIG. 7B shows an expanded view of the voltage trace of FIG. 7A. The signal contains noise from dc light and other sources which is easily filtered out by the synchronous detection circuit of the present invention. FIG. 7C shows the detection of bubbles formed during and after start up. In order to prevent or minimize the detection of light from other sources, the bubble detector of the present invention may be located inside of a housing assembly (not shown) so that only light projected onto the fiber at the coupling point and reflected by bubbles or delaminations is detected by the detection circuitry. The wavelength of light used may also be chosen so as to eliminate unwanted noise. The optical detector of course will be compatible with the wavelength of light used.

Figure 8:
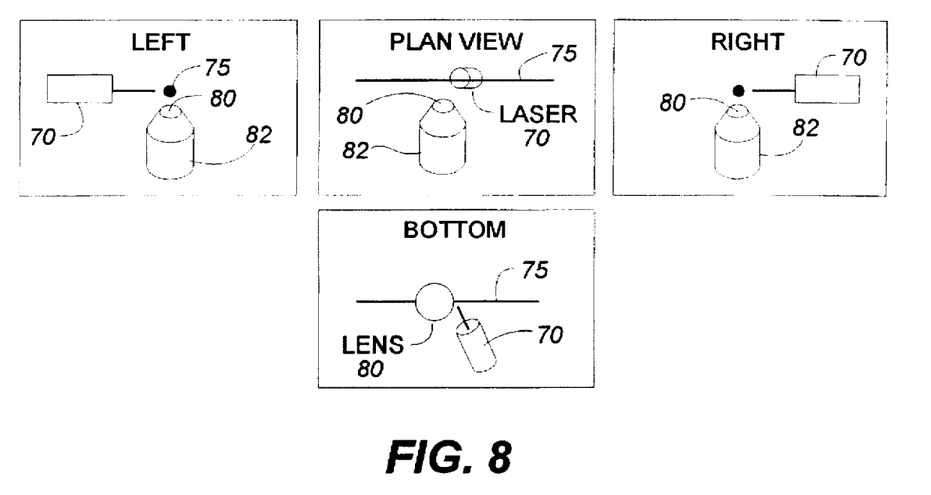
FIG. 8 illustrates an alternative embodiment of the present invention.

FIG. 8 illustrates an alternative embodiment of the present invention for detecting air bubbles, delaminations and other defects in an optical fiber. A light source 70, preferably a 900 nm narrowband infrared laser, projects light onto the optical fiber 75 at a preselected angle with respect to the longitudinal axis of the fiber 75. The angle of projection is almost perpendicular to the axis of the fiber and preferably is approximately 75°. A magnification lens 80 is positioned a preselected distance away from the coupling point adjacent a high speed photodetector 82. The photodetector 82 preferably is a reverse biased, gallium aluminum arsenide infrared photodetector (operating in the photoconductive mode). Light reflected by bubbles, delaminations or other defects contained in the fiber coating or between the fiber coating and the fiber itself is focused by lens 80 through a slit 85 onto photodetector 82.

Figure 9:
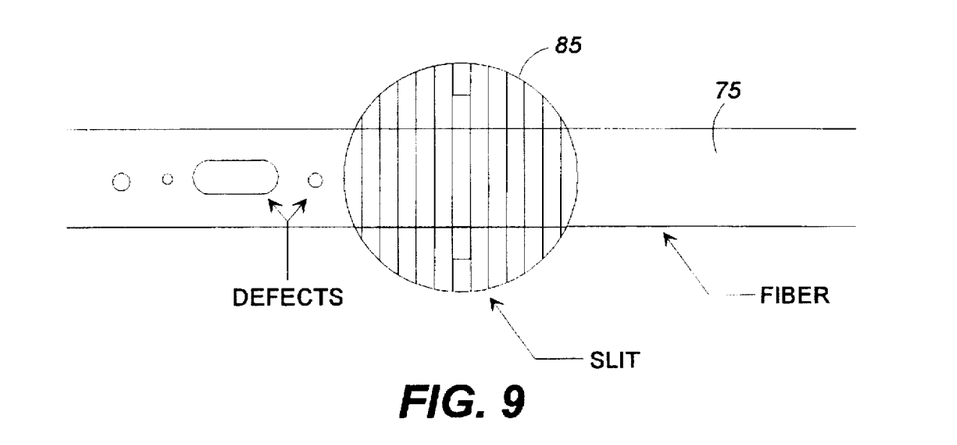
FIG. 9 illustrates an enlarged top view of the slit shown in FIG. 8.

FIG. 9 illustrates an enlarged top view of slit 85. Slit 85 preferably is approximately 50 micrometers in width. The amount of light detected by photodetector 82 will depend on the amount of light passing through slit 85 which, in turn, will depend on the size and type of defect detected. Therefore, the size and/or number of air bubbles, delaminations or other defects can be determined. Furthermore, the type of defects existing in the coating layers or between the primary coating and the fiber can be determined as well. In accordance with the present invention, it has been determined that the output of the photodetector will be different for air bubbles and delaminations. When delaminations are being detected, the output of the photodetector will undergo a voltage transition from high at the beginning of the delamination to low for the duration of the delamination to high at the end of the delamination. In contrast, when air bubbles are being detected, the output of the photodetector will be high when a bubble is present and low otherwise. Thus, the duration of the photodetector output signal as well as the magnitude of the output signal can be analyzed to determine the size and type of defect being detected.

Figure 10:
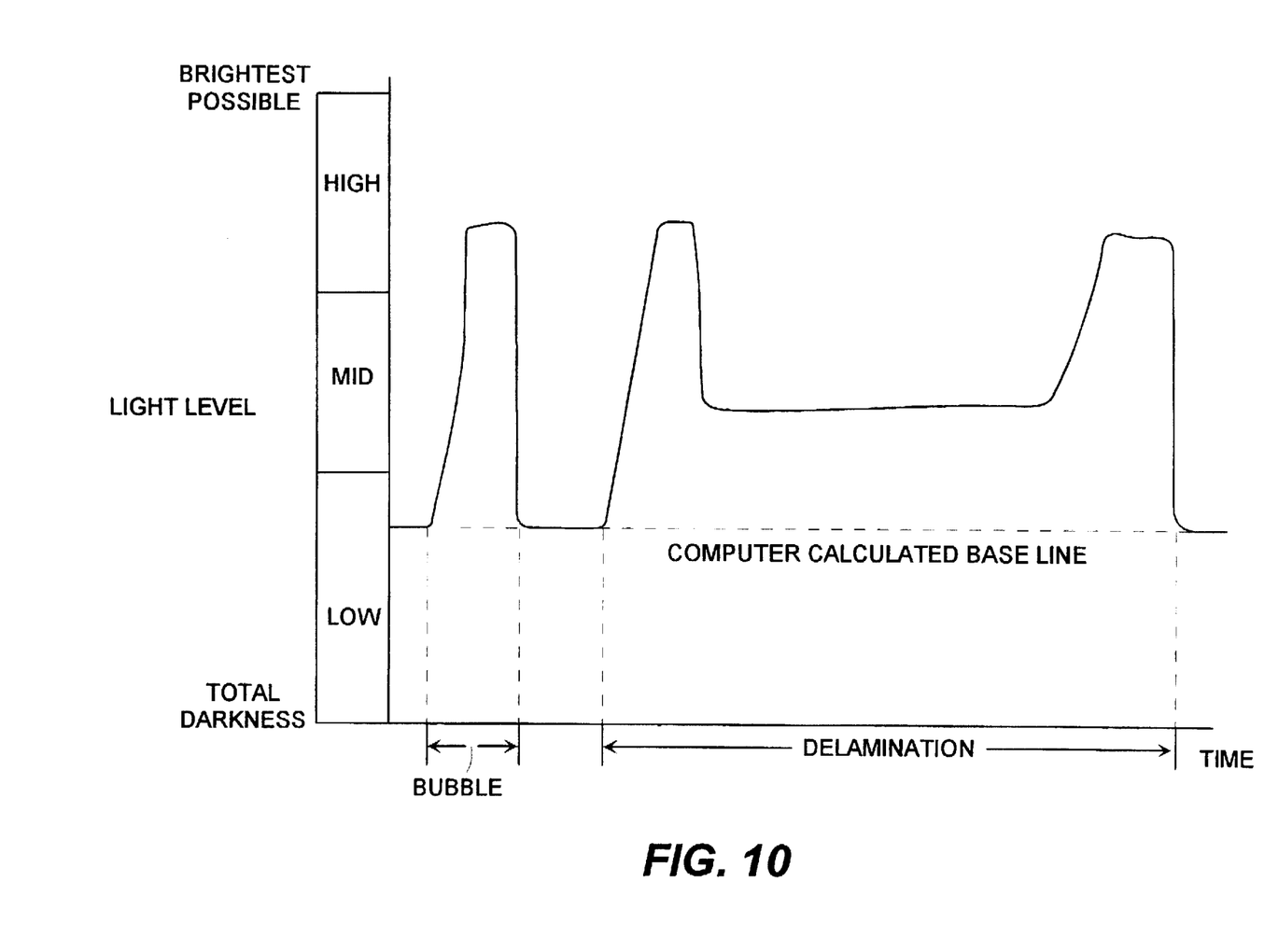
FIGS. 10A and 10B are flow charts illustrating the data acquisition process and defect determination process of the present invention in accordance with the embodiment shown in FIG. 8.

FIG. 10 is a plot of light intensity as a function of time which represents the output of photodetector in the time domain relative to a baseline voltage. The difference between the output of the photodetector when a bubble is detected as opposed to when a delamination is detected can readily be seen in the figure. When a bubble is detected, the light intensity increases from the low range to a maximum level in the high range for the duration of the bubble and then decreases until it returns to the baseline voltage. In contrast, when a delamination is detected, the light intensity increases from the low range to a maximum value in the high range at the leading edge of the delamination and then decreases to a level in the mid range which is greater than the baseline voltage but less than the maximum light level detected at the leading edge of the delamination. At the end of the delamination, the light intensity detected by the photodetector once again increases to its maximum level and then decreases to the baseline value. These characteristics are used to determine whether defects exist and, if so, the types of defects.

Figure 11A:
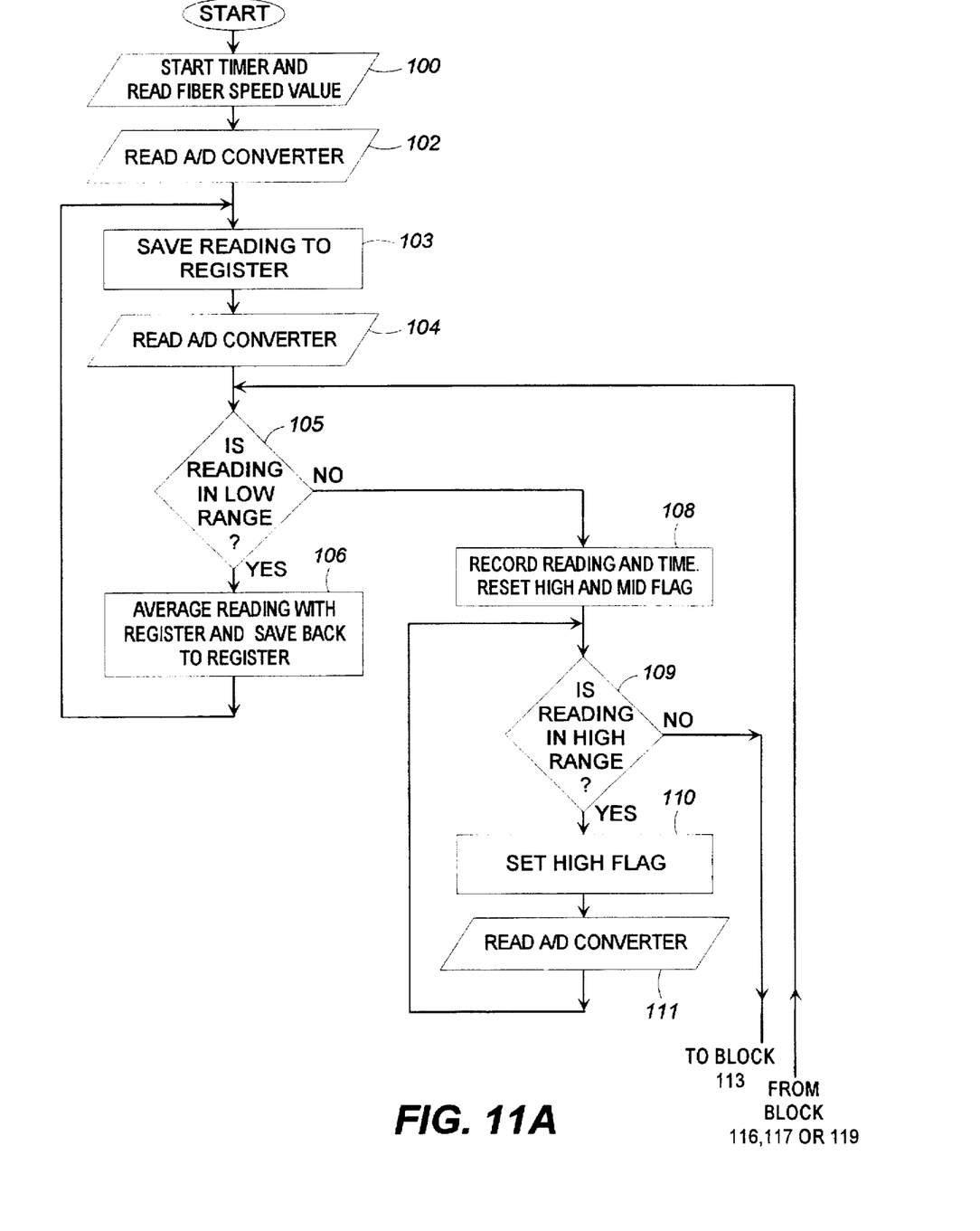
FIG. 11 is a block diagram of the detection and defect determination circuitry in accordance with the embodiment of FIG. 8.
Figure 11B:
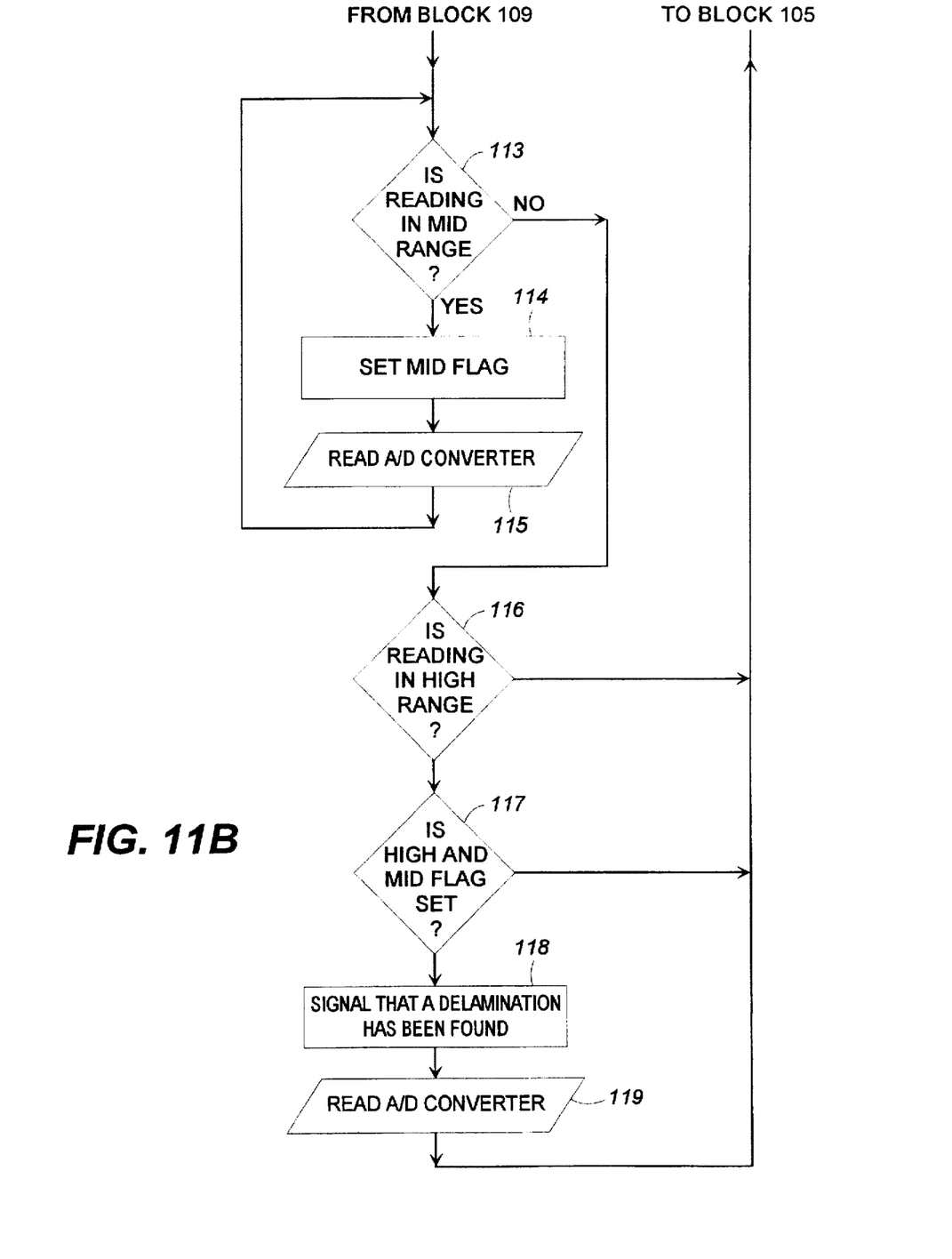

FIGS. 11A and 11B are flow charts illustrating the data acquisition and defect determination processes of the present invention in accordance with the embodiment of FIG. 8. As stated above, in order to determine the type of defect being detected, the fiber speed and the photodetector output as a function of time must be taken into account. In block 100, a timer is started and the fiber speed is stored in memory. The timer may be, for example, a counter which is periodically incremented. Blocks 102-106 correspond to a routine for establishing a baseline voltage which will be compared to the processed output of the photodetector for determining relative increases and decreases of the light intensity. Thus, blocks 102-106 correspond to a calibration routine.

In block 102, the analog-to-digital converter (ADC) which receives the output of the photodetector (see FIG. 12) is sampled. In block 103, the sampled output of the ADC is stored in memory. Preferably, the output of the ADC is stored in the accumulator of the microprocessor so that the data can be processed very quickly. In block 104, the ADC is sampled again. In block 105, a determination is made as to whether the sampled output of the ADC is in the low range. If the value is in the low range, the process proceeds to step 106 where the value is averaged with the value stored in the accumulator in block 106 and the average of the values is saved in the accumulator in step 103. The averaged value saved in the accumulator corresponds to the baseline voltage shown in FIG. 10.

By averaging the digitized output of the photodetector when the values are in the low range, small variations in light intensity, which may be the result of noise, are ignored. In block 105, if the value obtained from the ADC in block 104 is not in the low range, the value of the ADC and the time at which the ADC is sampled are stored in memory in step 108. A delamination flag, described in more detail below, is reset at this point in the process. When the value of the ADC is not in the low range, the system determines that a defect has been detected. In block 109, a determination is made as to whether the sampled value is in the high range. If so, the process proceeds to step 110 where the "high" flag is set. The ADC is then sampled again in step 111 and the process returns to step 109 where a determination is again made as to whether the sampled value of the ADC is in the high range. The process continues in the loop defined by blocks 109-111 until the sampled value of the ADC is no longer in the high range. When a determination is made at step 109 that the value of the ADC is not in the high range, the process proceeds to step 113 where a determination is made as to whether the value of the ADC is in the mid range. If the value of the ADC is in the mid range, then the system determines that a delamination is being detected. The mid range flag is then set in step 114 and the ADC is again sampled in step 115. The process continues in the loop defined by blocks 113-115 until a determination is made in block 113 that the sampled value of the ADC is no longer in the mid range.

Once a determination has been made in block 113 that the value of the ADC is no longer in the mid range, the process proceeds to block 116 where a determination is made as to whether the value of the ADC is in the high range. If the value of the ADC is in the high range, a determination is made at block 117 as to whether the high and mid range flags have previously been set. If so, the system determines that a delamination has been detected and an indication is provided at block 118. A defect attribution set may also be stored in memory at this point which corresponds to the type of defect detected. If a determination is made at block 1 16 that the value of the ADC is not in the high range, the process returns to step 105 where the process starts over. If a determination is made at block 116 that the value of the ADC is in the high range, and then a determination is made at block 117 that the high and mid range flags have not previously been set, then the system determines that a bubble, as opposed to a delamination, has been detected. The process then returns to block 105.

Figure 12:
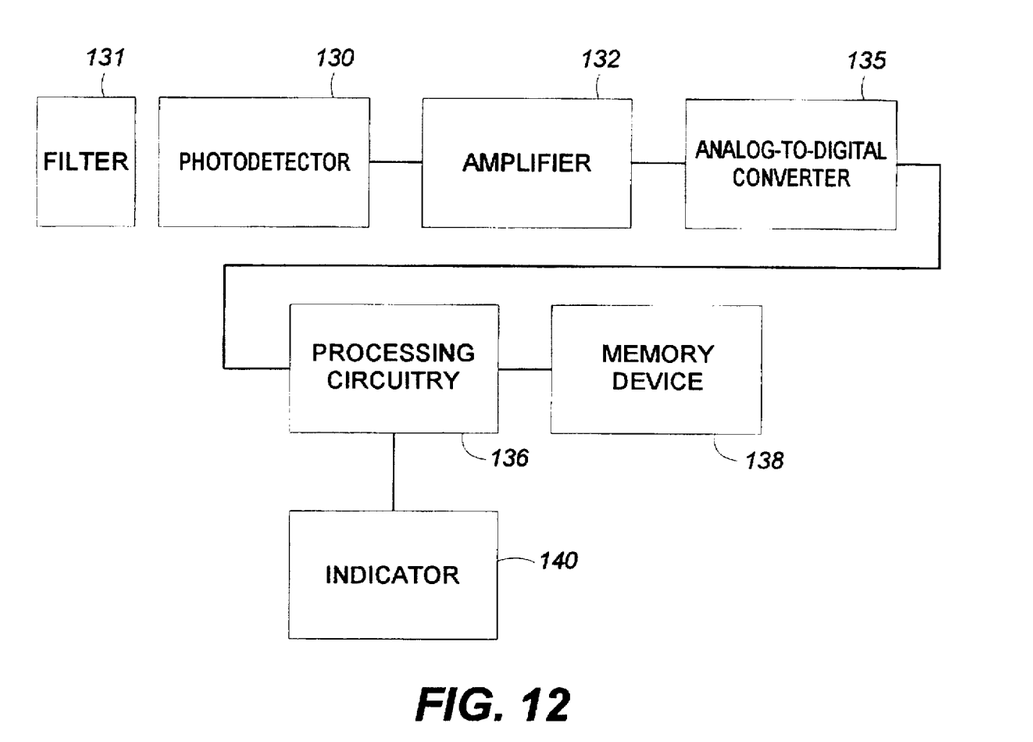
FIG. 12 is a plot of light intensity as a function of time obtained from the using the system shown in FIG. 8.

FIG. 12 is a block diagram of the detection and defect determination circuitry of the embodiment shown in FIG. 8 which performs the data acquisition and defect determination routines shown in FIGS. 11A and 11B. A reverse biased photodetector 130 detects the light reflected by defects in the fiber. As stated above, the photodetector preferably is a gallium aluminum arsenide infrared detector with a band width of 900 nanometers. Preferably, a visible light filter 131 is coupled to the photodetector 130 for filtering out visible light. The output of photodetector 130 is input to a high-bandwidth, high-gain DC-coupled transimpedance amplifier 132. The amplifier converts the current signal output from the photodetector 130 into a voltage signal. The amplified voltage signal output from amplifier 132 is input to analog-to-digital converter (ADC) 135, which preferably samples the output of amplifier 132 at a rate of 40 MHz.

The digital signal produced by ADC 135 is provided to processing circuitry 136 which may comprise, for example, an Intel 80486 microprocessor operating at 100 MH. The microprocessor is programmed with software for processing the output of ADC 135 to determine the types of defects detected by photodetector 130. The software preferably performs the routines discussed above with respect to FIGS. 11A and 11B. However, it will be apparent to those skilled in the art that software capable of accomplishing the goals of the present invention can be written in a variety of different ways and that the present invention is not limited to routines discussed above. The output of the processing circuitry 136 preferably is coupled to a flaw annunciator 140 which provides an indication that a flaw has been detected and the type of flaw detected. The processing circuitry 136 is coupled to a memory device which serves as a data logger by storing all of the information relating to the output of photodetector 130 including a time domain representation of the output of photodetector 130. The processing circuitry 136 must be sufficiently fast so that it is capable of analyzing the digital signals from ADC 135 in real time.

It should be noted that although the present invention has been described with respect to particular embodiments, the present invention is not limited to these embodiments. It should also be noted that modifications and alterations to the method and system of the present invention can be made without deviating from the spirit and scope of the present invention. For example, it will be apparent to those skilled in the art that components other than those discussed above can be used to construct the system of the present invention. The type of optical detector used can be any type suitable for detecting defects in the fiber. For example, a photodiode or a charge coupled device (CCD array) may be used to detect the defects. A frame grabber may also be used in conjunction with the photodetector to capture images of the fiber from which a determination will be made as to the existence or nonexistence of defects. It will also be also be apparent to those skilled in the art that methods other than those discussed above can be used to accomplish the goals of the present invention which are within the spirit and scope of the present invention. For example, it will be apparent to those skilled in the art that the optical fibers can be inspected after the primary coating layer has been applied but before the secondary coating has been applied, although the optical fibers preferably are inspected after both the primary and secondary coating layers have been applied. It should also be noted that the number of and/or the arrangement of the light sources and detectors can be modified so that optimum lighting and detection conditions are obtained.

What is claimed is:

1. An apparatus for detecting defects in a coating layer of an optical fiber, said apparatus comprising:

a light source for coupling a beam of light into the coating layer at a coupling spot along the optical fiber, said light source being positioned so that the beam of light is coupled into the coating layer at a preselected angle with respect to a longitudinal axis of the optical fiber;

an optical detector positioned adjacent the optical fiber a predetermined distance away from the coupling spot wherein the coupling spot is between said light source and said optical detector so that detection of light reflected at the coupling spot from an outer surface of the coating layer is avoided, and wherein said optical detector receives at least a portion of the light coupled into the coating layer by said light source as the light coupled into the coating layer is reflected outward from the optical fiber by defects existing in the coating layer; and a signal processor electrically coupled to said optical detector for receiving an output signal from said optical detector and for processing the output signal to determine whether or not one or more defects have been detected.

2. An apparatus according to claim 1 wherein the preselected angle is in the range of 5° to 30°.

3. An apparatus according to claim 1 wherein the light source is a laser.

4. An apparatus according to claim 1 wherein said optical detector is positioned on the same side of the optical fiber as is the light source.

5. An apparatus according to claim 1 wherein said signal processor is electrically coupled to the light source and wherein the light source is switched on and off at a predetermined switching frequency and wherein said signal processor takes the difference between the output of the optical detector when the light source is switched on and when the light source is switched off over a predetermined number of cycles of the switching frequency and averages the difference values and determines whether defects exist on the basis of the average.

6. An apparatus according to claim 1 wherein the determination as to whether defects have been detected is used in an optical fiber manufacturing process to prevent or minimize the occurrence of defects in optical fibers being produced in the manufacturing process.

7. An apparatus according to claim 1 wherein the coating layer has a refractive index and wherein the preselected angle is chosen in accordance with Snell's Law so that light coupled into the coating layer is refracted by the coating layer so that it travels within the coating layer in a direction substantially parallel to the longitudinal axis of the optical fiber.

8. An apparatus for detecting air bubbles in primary and secondary coating layers of an optical fiber and for detecting delaminations between the primary coating layer and the optical fiber, said apparatus comprising:

a light source for projecting a substantially collimated beam of light onto the secondary coating layer at a preselected angle in the range of 5° to 30° with respect to a longitudinal axis of the optical fiber at a coupling spot on the outer surface of the secondary coating layer;

a switching circuit electrically coupled to said light source for switching said light source off and on at a predetermined rate;

an optical detector positioned adjacent the coupling spot a predetermined distance away from the coupling spot for receiving light reflected by air bubbles contained in the primary and secondary coating layers and delaminations existing between the primary coating layer and the optical fiber and for producing an output signal in response to the reflections from the air bubbles and delaminations;

a signal processor for processing the output of said optical detector, said signal processor being synchronized with said switching circuit such that said signal processor samples the output of said optical detector at a rate related to said predetermined rate to obtain a set of samples, and wherein said signal processor determines whether or not bubbles or delaminations exist on the basis of the set of samples obtained.

9. An apparatus according to claim 8 wherein said light source is a laser.

10. An apparatus according to claim 8 wherein said optical detector is positioned on the same side of the optical fiber as is the light source.

11. An apparatus according to claim 8 wherein the secondary coating layer has a refractive index and wherein the preselected angle is chosen in accordance with Snell's Law so that light projected onto the secondary coating layer is refracted by the secondary coating layer so that it travels within the primary and secondary coating layers in a direction substantially parallel to the longitudinal axis of the optical fiber.

12. A method for inspecting optical fibers to detect air bubbles formed in coating layers of an optical fiber and to detect delaminations formed between one of the coating layers and the fiber, said method comprising the steps of:

coupling a substantially collimated beam of light into an optical fiber coating layer at a preselected angle in the range of 5 to 300 with respect to a longitudinal axis of the optical fiber, wherein the substantially collimated beam of light is coupled into an outer surface of the coating layer at a coupling spot;

positioning an optical detector near the optical fiber a predetermined distance from the coupling spot, wherein said optical detector receives light coupled into the coating layer which is reflected by air bubbles or delaminations toward said optical detector, wherein said optical detector outputs electrical signals in response to light received by said optical detector;

processing the electrical signals output from said optical detector to obtain a processed signal and analyzing the processed signal to determine whether or not air bubbles or delaminations have been detected.

13. The method of claim 12 wherein the angle of projection of the substantially collimated beam of light with respect to the longitudinal axis of the fiber is in the range of between 10° to 20°.

14. The method of claim 12 wherein the coating layer has a refractive index and wherein the preselected angle is chosen in accordance with Snell's Law so that light projected onto the coating layer is refracted by the coating layer so that it travels within the coating layer in a direction substantially parallel to the longitudinal axis of the optical fiber.

15. The method of claim 12 wherein light is coupled into the coating layer by a laser which is switched on and off at a predetermined frequency and wherein the processing step includes synchronizing the switching of the laser by sampling the output of said optical detector at a rate related to said predetermined frequency to obtain a set of samples, and wherein the processing step includes determining whether or not bubbles or delaminations exist on the basis of the set of samples obtained.

16. The method of claim 12 wherein the optical detector is located adjacent the optical fiber on the same side of the optical fiber at which the coupling spot is located at a distance of between about 1 millimeter and 10 centimeters from the coupling spot.

17. The method of claim 12 wherein said method is incorporated into an optical fiber manufacturing process and wherein after the optical fiber has been inspected for air bubbles and delaminations the optical fiber is taken up on a first take-up roll or a second take-up roll depending on whether air bubbles or delaminations have been detected in the optical fiber, wherein if a determination is made during the processing step that air bubbles or delaminations do not exist, the optical fiber is taken up on the first take-up roll, and wherein if a determination is made during the processing step that air bubbles or delaminations do exist, the optical fiber is taken up on the second take-up roll.

* * * * *